United States Patent [19]
Atsumi et al.

[11] Patent Number: 4,560,750
[45] Date of Patent: Dec. 24, 1985

[54] CEPHEM COMPOUNDS AND PROCESS FOR PREPARING THE SAME

[75] Inventors: Kunio Atsumi; Kiyoaki Katano, both of Yokohama; Fumio Kai, Fujisawa; Ken Nishihata; Eiichi Akita, both of Yokohama, all of Japan

[73] Assignee: Meiji Seika Kaisha Ltd., Tokyo, Japan

[21] Appl. No.: 367,016

[22] Filed: Apr. 9, 1982

[30] Foreign Application Priority Data

Apr. 13, 1981 [JP] Japan ................................ 56-54275

[51] Int. Cl.$^4$ .................. C07D 501/57; A61K 31/545
[52] U.S. Cl. ........................................ 544/21; 544/26; 544/27
[58] Field of Search ............................. 544/21, 26, 27; 424/246

[56] References Cited

U.S. PATENT DOCUMENTS

| | | | |
|---|---|---|---|
| 4,008,229 | 2/1977 | Spitzer | 544/21 |
| 4,162,251 | 7/1979 | Hiraoka et al. | 544/21 |
| 4,260,746 | 4/1981 | Taylor et al. | 544/21 |
| 4,317,907 | 3/1982 | Saikama et al. | 544/21 |

OTHER PUBLICATIONS

Atsumi et al., Tetrahedron Letters, vol. 23, No. 29, pp. 2977–2980 (1982).
Communications to the Editor, pp. 2401–2403; Baldwin et al.
J. Org. Chem., vol. 38, No. 5, 1973, pp. 943–950; Slusarchyk et al.
Tetrahedron Letters No. 31, pp. 2705–2708, 1975, Pergamon Press; Yanagisawa et al.
Tetrahedron Letters No. 16, pp. 1307–1310, 1976, Pergamon Press; Sugimura et al.
Communications to the Editor, pp. 5505–5507; Kobayashi et al.
Journal of the American Chemical Society/94:4/2/23/72; pp. 1408–1410; Cama et al.

Primary Examiner—Nicholas S. Rizzo
Attorney, Agent, or Firm—Schwartz, Jeffery, Schwaab, Mack, Blumenthal & Evans

[57] ABSTRACT

Disclosed is a novel cephem compound represented by the formula:

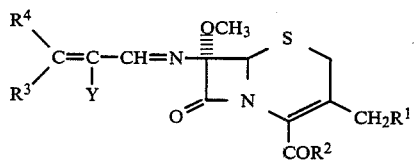

wherein $R^1$, $R^2$, $R^3$, $R^4$ and Y are as defined in the specification, which is a useful intermediate for synthesizing various cephalosporin antibiotics having a methoxy group at the 7α-position thereof. Also disclosed is a process for preparing the same.

7 Claims, No Drawings

CEPHEM COMPOUNDS AND PROCESS FOR PREPARING THE SAME

This invention relates to a new class of cephem derivatives and a process for preparing the same. More particularly, it relates to a cephem compound which is a new synthetic intermediate useful for various cephalosporin antibiotics having a methoxy group at the 7α-position thereof and a new process for preparing the said cephem compound. Still more particularly, this invention can provide a cephem compound having a methoxy group at the 7α-position thereof and a new process for introducing a methoxy group into a cephalosporin moiety at the 7α-position thereof.

As a group of cephalosporin-type antibiotic substances having a methoxy group at the 7α-position thereof, cephamycin-type antibiotics have been found to be naturally present and they have also been found to exhibit an excellent antibiotic activity upon the characteristic chemical structure of having a methoxy group at the 7α-position thereof. Since then, there have been synthesized many 7α-methoxycephalosporin derivatives. On the other hand, various studies have been made on a new process for chemically introducing a methoxy group into a cephem ring at the 7α-position thereof.

Some of these new derivatives have already been given with an established evaluation as an excellent antibiotic substance and practically applied as a chemotherapeutic agent for clinical use. Accordingly, a chemical process for introducing a methoxy group into a cephalosporin skeleton at the 7α-position thereof has been regarded as being commercially of utmost importance and there have hitherto been proposed various processes therefor. Illustrative examples thereof may include the following processes:

(1) The process, namely acylimine process, wherein a 7(or 6)-acylaminocephalosporin (or penicillin) is reacted with a positive halogen compound such as tert-butylhypochlorite in the presence of a strong base to form the corresponding acylimino compound followed by addition of methanol to the so formed compound (J. Am. Chem. Soc., 95 2401 (1973)).

(2) The process, namely carbanion process, wherein the amino group at the 7(or 6)-position is converted to Schiff base, the corresponding carbanion at the 7(or 6)-position is formed from the Schiff base by the action of a strong base, the said carbanion is reacted with a methanethiosulfonate or a positive halogen compound to form a 7α(or 6α)-methylthio-or halo derivative and then the latter derivative is converted to the corresponding 7α(or 6α)-methoxy derivative with methanol (J. Org. Chem., 38, 943 (1973)).

(3) The methoxy-introducing process wherein the Schiff base of the 7(or 6)-amino group with 3,5-di-tert-butyl-4-hydroxybenzaldehyde is oxidized to the quinoneimine form and then methanol is added to the said imine form (Tetrahedron Letters., 1975, 2705).

(4) The process wherein an α-halo- or α,α-dihaloacetamidocephalosporin (or penicillin) or the vinylog thereof is converted to the corresponding iminohalogenated form, the imino ether is derived from the latter form by the substitution of the halogen with methanol, the said imino ether is converted to the corresponding vinyl imine by a 1,4-dehydrohalogenation reaction with a strong base and 1,4-addition of methanol to the said vinyl imine is conducted to introduce a methoxy group at the 7α(or 6α)-position thereof (Tetrahedron Letters., 1976, 1307).

(5) The process wherein a 7(or 6)-sulfenamidocephalosporin (or penicillin) is oxidized to the corresponding sulfenimine derivative and methanol is added to the said derivative (J. Am. Chem. Soc. 99, 5505 (1977)).

(6) The process comprising diazotization of the 7(or 6)-amino group and subsequent addition reaction of an azide compound, e.g., a halogen azide to the diazo form (J. Am. Chem. Soc., 94, 1408 (1972)).

However, the above-recited process are not always said to be complete without any defaults and it is the present situation that there have been made continuous studies on a variety of new or improved processes for a industrially satisfactory process.

For instance, the above processes have the following defects or difficulties and hence there has been desired a development in a far more excellent process.

The above process (1) has a defect that any oxidized by-products tend to be produced owing to the strong oxidizing agent employed if there is present a side-chain liable to be oxidized, in particular, a side-chain containing a sulfide bond. The above processes (1), (2) and (4) involve difficult points that a specific reaction condition such as an extremely low temperature for the reaction (namely, $-78°$ C.) should be required and a strong base, such as lithium methoxide and the like should be employed, which may readily cause a β-lactam ring cleavage. The above processes (3) and (5) involve heterogenous reaction employing a large excess of a metal oxide (namely, a solid phase), but the processes show such a difficult point that it is difficult to control such heterogenous reaction if practised in an industrial scale. The above process (6) shows such defects that addition of the azide compound is not stereo-selective, with a yield being poor, that long and complicated reaction pathway is needed and so on.

The present inventors have made extensive studies for a new methoxylation reaction which may be practised under a mild reaction condition by way of simple reaction procedures with high selectivity and efficiency and, as a result, have found out a new process involving a novel 7α-methoxylation reaction, as illustrated by the following reaction equation:

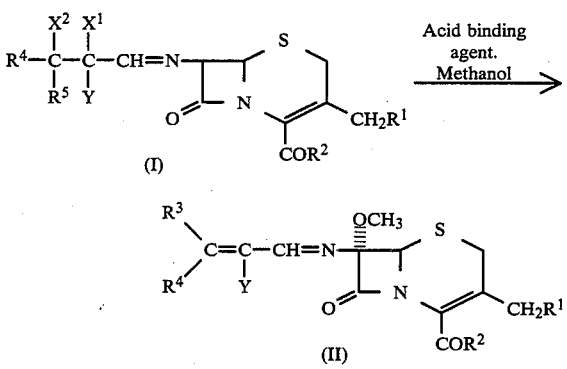

On the above formulae, $R^1$ represents a hydrogen atom or a group of —A—B in which A is an oxygen atom or a sulfur atom and B is an acyl group; a substituted or unsubstituted heterocyclic group containing as a ring atom at least one hetero atom selected from the group consisting of an oxygen atom, a nitrogen atom and a sulfur atom; or a substituted or unsubstituted carbamoyl group: $R^2$ is a hydroxy group or a carboxyl-protecting group: $R^3$ and $R^4$ may be the same or different and each represent a hydrogen atom, a lower alkyl group or a substituted or unsubstituted phenyl group: Y represents a halogen atom, a lower alkyl group or a substituted or unsubstituted phenyl group: and $X^1$ and $X^2$ may be the same or different and each represent a halogen atom.

As the acyl group which is one embodiment of B in the $R^1$, there may be, for example, mentioned an acetyl group, an acetoacetyl group and the like. As the substituent which may be on the heterocyclic group, another embodiment of B in the $R^1$, there may be, for example, mentioned a lower alkyl group, an aminoalkyl group, a carboxyalkyl group, a sulfoalkyl group and the like. Illustrative examples of such heterocyclic group may include, for example, a 1H-tetrazol-5-yl group, a 1-methyl-1H-tetrazol-5-yl group, a 1-carboxymethyl-1H-tetrazol-5-yl group, a 2-carboxymethyl-1H-triazol-5-yl group, a 1-sulfoethyl-1H-tetrazol-5-yl group, a 2-carboxymethyl-1-methyl-1H-triazol-5-yl group, a 4-methyl-5-oxo-6-hydroxy-4,5-dihydro-1,2,4-triazin-3-yl group a pyridiniummethyl group, a triazolyl group, a thiadiazolyl group and the like. As the substituted carbamoyl group, there may be mentioned, for example, a mono-substituted or disubstituted carbamoyl group and the like, said substituent being, for example, an alkyl group.

The $R^2$ may be a hydroxy group or a carboxyl-protecting group and, as the protecting group for the carboxyl group, there may be optionally employed any of those protecting groups ordinarily used in penicillin and cephalosporin field: For example, there may be mentioned a benzhydryloxy group, a tert-butoxy group, a p-nitrobenzyloxy group, 2,2,2-trichloroethoxy group, a methoxymethoxy group and the like. As the halogen atom represented by $X^1$ and $X^2$, there may be mentioned chlorine, bromine, iodine.

More specifically, the present end compound of the formula (II), a new 7α-methoxycephem compound, can be prepared by subjecting the Schiff base of the formula (I) to the action of an acid binding agent in the presence of methanol, the said Schiff base being formed from a 7-aminocephem compound of the formula (III):

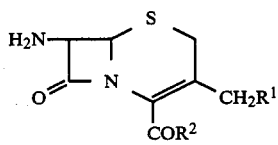

(III)

(wherein $R^1$ and $R^2$ are as defined above) and a 2,2,3-trihaloaldehyde, 2-lower alkyl-2,3-dihaloaldehyde or 2-substituted or unsubstituted phenyl-2,3-dihaloaldehyde of the formula (IV):

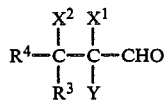

(IV)

(wherein $R^3$, $R^4$, Y, $X^1$ and $X^2$ are as defined above).

The reaction starting from the compound (I) to the compound (II) can be conducted in methanol or an organic solvent containing methanol usually, at room temperature or lower. The reaction temperature may be, however, selected and applied optionally upon a sort of the acid binding agent as employed.

As the acid binding agent which may be employed in the present process, there may be mentioned, for example, a basic inorganic salt such as borax, potassium carbonate and sodium carbonate; a solid acid binding agent such as silica gel, alumina, a molecular sieve and a basic resin; a metal alkoxide such as lithium methoxide and potassium tert-butoxide; an alkali (or alkaline-earth) metal hydroxide; an alkali (or alkaline-earth) metal oxide; a metal amide such as lithium diisopropylamide; an alkali metal hydride such as sodium hydride; an alkyl metal such as alkyl lithium; a tertiary amine such as triethylenediamine, diazabicyclononene (DBN), diazabicycloundecene, diisopropylethylamine and pyridine; and so on. Most preferable are, for example, borax, potassium carbonate, lithium methoxide, alumina and the like.

It is at least requisite that 2 equivalents of the base as the said acid binding agent be employed to 1 mole of the compound (I) and, usually, 3 equivalents or a large excess of the base may be employed. If any strong base is to be employed, the reaction temperature should preferably be as low as possible, since such side reaction as cleavage of the β-lactam ring may be highly apt to occur by the action of a base. Depending upon a sort of the base employed, the reaction may be suitably effected at a proper range of temperature; for instance, at room temperature to ice-cooling temperature where borax or potassium carbonate is used, at −20° C. to ice-cooled temperature where alumina is used, at below −50° C., preferably below −78° C., where lithium methoxide is used.

The Schiff base (I) which may be employed as a starting material in the present process can be prepared from the 7-aminocephem compound (III) and the aldehyde (IV) in a conventional manner. Where the Y is to be a halogen atom, the Schiff base (I) may be also prepared by the reaction of an addition compound of the formula (V):

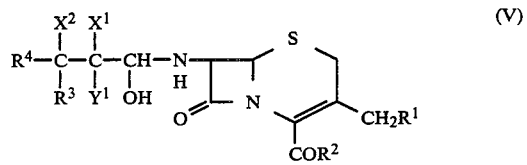

(V)

(wherein $Y^1$ is a halogen atom and $R^1$, $R^2$, $R^3$, $R^4$, $X^1$ and $X^2$ are as defined above), which is formed from a 7-aminocephem compound (III) and the 2,2,3-trihaloaldehyde of the formula (IV) wherein Y is a halogen atom, with a halogenating agent such as a sulfur halide, a phosphorous halide or an oxide thereof, e.g., thionyl chloride, phosphorus pentachloride, phosphorus oxychloride, in the presence of an organic tertiary amine such as dimethylaniline and pyridine.

The reaction in the present process is a novel reaction unlike prior art reactions and the reaction wherein release of 2 moles of a hydrogen halide from the starting compound (I) can occur together with addition of 1 mole of methanol to form the compound (II) eventually as a stable final product. The present reaction does not always require the use of a strong base liable to induce cleavage of a β-lactam ring as seen in prior art methoxylation, nor does the use of a strong oxidizing agent readily forming by-products and the use of reaction condition and reagent readily accompanying isomerization, but our reaction may advantageously proceed under a mild condition to accomplish the desired 7α-methoxylation with easy recovery of the product and high efficiency.

Moreover, the present compound (II) is particularly useful as an intermediate for the synthesis of various 7α-methoxycephalosporin derivatives, because the aldehyde moiety can be very easily released from the compound (II) as discussed hereinbelow. Namely, the compound (II) can be readily treated with a substituted hydrazine such as Girard's reagent ("Reagents for Organic Synthesis", p 410, Fieser & Fieser, 1967) to release the vinylaldehyde moiety of the Schiff base (II) very easily, thereby producing a 7β-amino-7α-methoxycephem compound of the formula (VI):

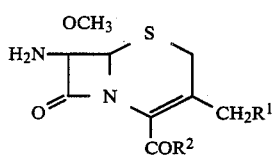

(wherein $R^1$, $R^2$ are as defined above). The compound (VI) thus produced is subjected to the reaction with, for example, a haloacetyl halide of the formula (VII):

$$X^3CH_2COX^4 \quad (VII)$$

(wherein $X^3$ and $X^4$ may be the same or different and each represents a halogen atom) in a conventional manner to yield a 7β-haloacetylamino-7α-methoxy cephem compound of the formula (VIII):

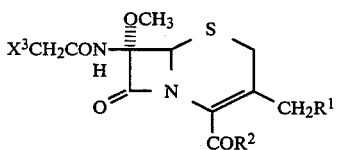

(wherein $R^1$, $R^2$, $X^3$ are as defined above). Generally, both the compounds (VI) and (VIII) are known and, for example, the compound (VI) may be converted in a well-known manner (The Journal of Anbibiotics, XXIX, 554 (1976)) to the useful 7α-methoxycephalosporin antibiotic substance, i.e. 7β-(cyanomethylthioacetamide)-7α-methoxy-3-[(1-methyl-1H-tetrazol-5-yl)thiomethyl]-3-cephem-4-carboxylic acid. Also, the compound (VIII) wherein, for example, $X^3$ is Br, $R^1$ is

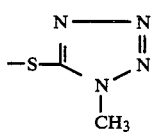

and $R^2$ is —O—CH(C₆H₅)₂ may be converted in a well-known manner (Japanese Laid-Open Patent Application No. 83791/1980) to the useful 7α-methoxycephalosporin, i.e. 7β-[(2(R)-2-amino-2-carboxyethyl)thioacetamido]-7α-methoxy-3-[(1-methyl-1H-tetrazol-5-yl)thiomethyl]-3-cephem-4-carboxylic acid.

This invention will be more fully illustrated by way of the following Synthesis Examples and Examples.

SYNTHESIS EXAMPLE 1

Benzhydryl 7β-(2',3'-dibromo-2'-chlorobutylideneamino)-3-(1-methyl-1H-tetrazol-5-yl)thiomethyl-3-cephem-4-carboxylate

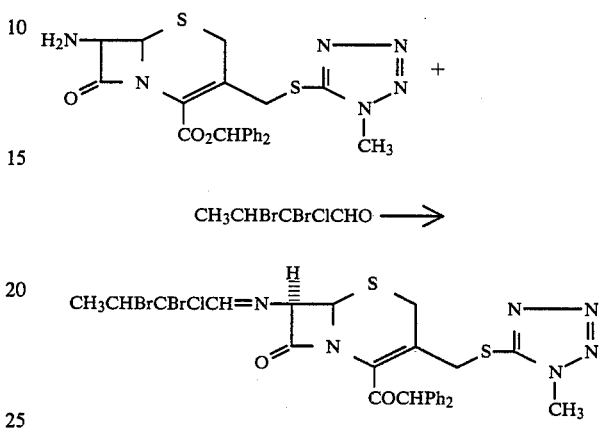

To a solution of benzhydryl 7β-amino-3-(1-methyl-1H-tetrazol-5-yl)thiomethyl-3-cephem-4-carboxylate (4.95 g, 10.0 mmol) in methylene chloride (70 ml) was added under ice-cooling a solution of 2,3-dibromo-2-chlorobutanal (See F. D. Chattaway, H. Irring and G. H. Outhwaite, J. Chem. Soc., 993, (1933)) (2.64 g, 10 mmol) in methylene chloride (5 ml) and then the mixture was stirred for one hour. The reaction mixture was cooled to −20° C., N,N-dimethylaniline (7 ml) was added thereto and thionyl chloride (0.8 ml, 11 mmol) was added dropwise. After stirring under ice-cooling for one hour, the reaction mixture was poured into ice-water and, after shaking, the methylene chloride layer was separated. The aqueous layer was extracted with methylene chloride (30 ml), the extract was combined with the previously separated methylene chloride layer and the combined organic layer was washed successively with a mixture of a saturated potassium hydrogen sulfate solution (30 ml) and ice (30 g) three times, ice-water (30 ml), and then a mixture of a saturated sodium hydrogen carbonate solution (30 ml) and ice (30 g). After drying over anhydrous magnesium sulfate, the mixture was at immediately concentrated under reduced pressure to leave a foamy residue. The residue was crystallized with the addition of ice-cooled ethyl acetate (20 ml) and then the so obtained crystalline substance was recovered by filtration and dried under reduced pressure to yield 5.19 g (70%) of the title compound. This product gradually decomposed with coloration at 75° C. and higher.

IR (KBr tablet method) cm⁻¹: 1782, 1716

NMR (CDCl₃), δ ppm: 2.05 (3H, d, J=7 Hz), 3.65 (2H, broad s), 3.77 (3H, s), 4.13 (1H, d, J=14 Hz), 4.41 (1H, d, J=14 Hz), 4.6~4.9 (1H, m), 5.05 (1H, d, J=5 Hz), 5.36 (1H, dd, J=5 Hz, 2 Hz), 6.82 (1H, s), 7.1~7.5 (10H, broad s), 8.03+8.09 (1H, d+d, J=2 Hz).

SYNTHESIS EXAMPLE 2 tert-Butyl 7β-(2',3'-dibromo-2'-chlorobutylideneamino)-3-acetoxymethyl-3-cephem-4-carboxylate

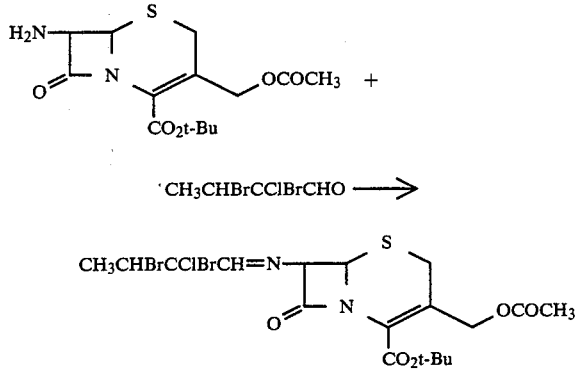

To a solution of tert-butyl 7β-amino-3-acetoxymethyl-3-cephem-4-carboxylate (1.642 g, 5.000 mmol) in methylene chloride (35 ml) was added under ice-cooling a solution of 2,3-dibromo-2-chlorobutanal (1.642 g, 5.000 mmol) in methylene chloride (3 ml) and the reaction mixture was stirred for one hour. The reaction mixture was cooled to −20° C., N,N-dimethylaniline (3.5 ml) was added thereto and then thionyl chloride (0.4 ml, 5.5 mmol) was added dropwise. After stirring under ice-cooling for one hour, the reaction mixture was poured into ice-water (30 ml) and, after shaking, the methylene chloride layer was separated. The aqueous layer was extracted with methylene chloride (20 ml) and the extract was combined with the previously separated methylene chloride layer. The combined organic layer was washed successively with a saturated aqueous solution of potassium hydrogen sulfate (20 ml, three times) under ice-cooling, ice-water (20 ml) and a saturated aqueous solution of sodium hydrogen carbonate (20 ml) under ice-cooling. After drying over anhydrous magnesium sulfate, the mixture was concentrated under reduced pressure. To the residue was added ether (30 ml), the mixture was stirred well and insolubles were filtered off. The filtrate was concentrated under reduced pressure again, the residue was washed with n-hexane (30 ml, three times) and dried under reduced pressure to yield 2.73 g (95%) of the title compound as a pale brown foamy substance.

IR (KBr tablet method) cm$^{-1}$: 1780, 1738, 1720.

NMR (CDCl$_3$) δ ppm: 1.56 (9H, s), 2.01 (3H, d, J=6 Hz), 2.03 (3H, s), 3.31 (1H, d, J=18 Hz), 3.53 (1H, d, J=18 Hz), 4.76 (1H, d, J=14 Hz), 4.65∼5.00 (1H, m), 5.15 (1H, d, J=14 Hz), 5.18 (1H, d, J=5 Hz), 5.50 (1H, dd, J=5 Hz, 2 Hz), 8.15+8.20 (1H, d+d, J=2 Hz).

SYNTHESIS EXAMPLE 3

Benzhydryl 7β-(2',2',3'-tribromopropylideneamino)-3-(1-methyl-1H-tetrazol-5-yl)thiomethyl-3-cephem-4-carboxylate

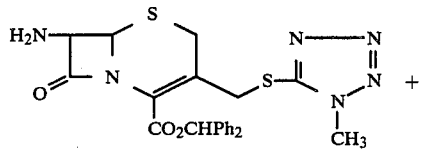

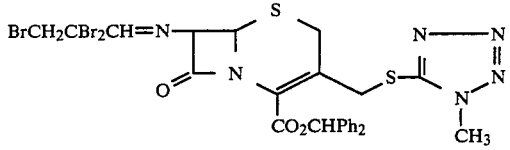

To a solution of benzhydryl 7β-amino-3-(1-methyl-1H-tetrazol-5-yl)thiomethyl-3-cephem-4-carboxylate (2.473 g, 5.000 mmol) in methylene chloride (35 ml) was added under ice-cooling a solution of 2,2,3-tribromopropanal (1.474 g, 5.000 mmol) in methylene chloride (5 ml) and the mixture was stirred for 20 minutes. The reaction mixture was cooled to −20° C., N,N-dimethylaniline (3.5 ml) was added thereto and then thionyl chloride (0.5 ml, 6.9 mmol) was added dropwise. After stirring under ice-cooling for 2 hours, the reaction mixture was poured into a mixture of a saturated aqueous solution of potassium hydrogen sulfate (100 ml) with ice (100 g) followed by extraction with methylene chloride (400 ml, twice). The methylene chloride layer was washed successively with an ice-cooled saturated aqueous solution of potassium hydrogen sulfate (200 ml) and then ice-water (200 ml). Thereafter, the organic layer was dried over anhydrous magnesium sulfate. The solvent was distilled off under reduced pressure and the residue was crystallized with the addition of ethyl acetate (20 ml). The crystalline substance was recovered by filtration, washed with a small volume of ice-cooled methylene chloride and dried under reduced pressure to yield 2.720 g (71%) of the title compound as a pale yellow crystal. This product gradually decomposed with coloration at 90° C. and higher.

IR (KBr tablet method) cm$^{-1}$: 1780, 1718.

NMR (CDCl$_3$) δ ppm: 3.67 (2H, broad s), 3.82 (3H, s), 4.20 (1H, d, J=14 Hz), 4.32 (2H, s), 4.43 (1H, d, J=14 Hz), 5.11 (1H, d, J=5 Hz), 5.42 (1H, dd, J=5 Hz, 2 Hz), 6.92 (1H, s), 7.33 (10H, broad s), 8.24 (1H, d, J=2 Hz).

SYNTHESIS EXAMPLE 4

Benzhydryl 7β-(2',2',3'-tribromo-3'-phenylpropylideneamino)-3-(1-methyl-1H-tetrazol-5-yl)thiomethyl-3-cephem-4-carboxylate

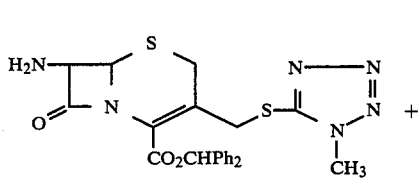

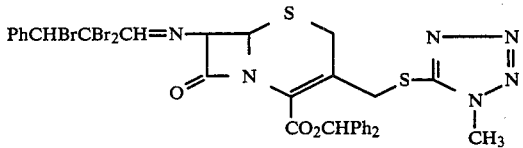

To a solution of benzhydryl 7β-amino-3-(1-methyl-1H-tetrazol-5-yl)thiomethyl-3-cephem-4-carboxylate (4.001 g, 8.09 mmol) in methylene chloride (70 ml) was added a methylene chloride solution of a crude 2,2,3-tribromo-3-phenylpropanal (3.00 g, 8.09 mmol), which was prepared by reacting α-bromocinnamaldehyde with an equimolar amount of bromine in carbon tetrachloride at 0°~5° C. for 3 days under ice-cooling. The reaction mixture was cooled to −20° C., N,N-dimethylaniline (6.5 ml) was added thereto and then thionyl chloride (0.7 ml) was added dropwise. After stirring at 0° C. for 30 minutes, the reaction mixture was washed successively with ice-water (40 ml), an ice-cooled saturated aqueous solution of potassium hydrogen sulfate (40 ml, twice) and ice-water (40 ml). The methylene chloride solution was dried over anhydrous magnesium sulfate and concentrated to dryness under reduced pressure to give 7.02 g of a brown foamy substance. Two grams of the substance thus obtained were separated by a silica gel column chromatography (200 g of silica gel, benzene:ethyl acetate = 10:1 as a developing solvent). The combined fractions of Rf=0.65 (benzene:ethyl acetate = 4:1) were concentrated to dryness and crystallized with the addition of ether (10 ml). The crystalline substance was recovered by filtration and dried under reduced pressure to yield 0.643 g (33%) of the title compound as a white crystal. This product decomposed with coloration over 95° C.

IR (KBr tablet method) cm$^{-1}$: 1790, 1721.

NMR (CDCl$_3$) δ ppm: 3.57 (2H, broad s), 3.64 (3H, s), 4.10 (1H, d, J=14 Hz), 4.31 (1H, d, J=14 Hz), 4.98 (1H, d, J=5 Hz), 5.29 (1H, dd, J=5 Hz, 2 Hz), 5.55+5.58 (1H, s+s), 6.80 (1H, s), 7.0~7.6 (15H, m), 8.03+8.11 (1H, d+d, J=2 Hz).

SYNTHESIS EXAMPLE 5

Benzhydryl 7β-(2′,2′,3′-trichlorobutylideneamino)-3-(1-methyl-1H-tetrazol-5-yl)thiomethyl-3-cephem-4-carboxylate

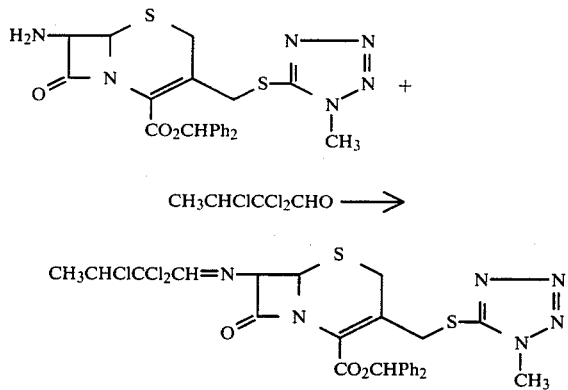

To a solution of benzhydryl 7β-amino-3-(1-methyl-1H-tetrazol-5-yl)thiomethyl-3-cephem-4-carboxylate (4.946 g, 10.000 mmol) in methylene chloride (70 ml) was added under ice-cooling a solution of butyl chloral (2,2,3-trichlorobutanal) (1.755 g, 10.000 mmol) in methylene chloride (5 ml) and Molecular Sieve 3A (15 g) was then added thereto. The reaction mixture was heated under reflux for 2 hours. Then, the reaction mixture was allowed to cool to room temperature and filtered. The filtrate was concentrated under reduced pressure to yield 5.41 g (83%) of the title compound as a pale brown foamy substance.

NMR (CDCl$_3$) δ ppm: 1.77 (3H, d, J=6 Hz), 3.69 (2H, broad s), 3.80 (3H, s), 4.20 (1H, d, J=14 Hz), 4.45 (1H, d, J=14 Hz), 4.50~5.00 (1H, m), 5.13 (1H, d, J=5 Hz), 5.42 (1H, dd, J=5 Hz, 2 Hz), 6.92 (1H, s), 7.31 (10H, broad s), 8.20+8.22 (1H, d+d, J=2 Hz).

SYNTHESIS EXAMPLE 6 tert-Butyl 7β-(2′,2′,3′-trichlorobutylideneamino)-3-methyl-3-cephem-4-carboxylate

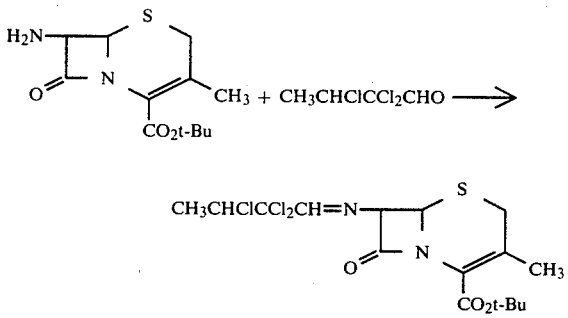

To a solution of tert-butyl 7β-amino-3-methyl-3-cephem-4-carboxylate (1.35 g, 5.00 mmol) in methylene chloride (30 ml) was added dropwise under ice-cooling butyl chloral (2,2,3-trichlorobutanal) (0.63 ml, 5.0 mmol). The reaction mixture was stirred at room temperature for 10 minutes, was allowed to cool to −20° C., N,N-dimethylaniline (3 ml) was added thereto and then thionyl chloride (0.5 ml) was added dropwise. After stirring under ice-cooling for 1.5 hours, the reaction mixture was poured into ice-water (40 ml), extracted with methylene chloride (30 ml, twice). The organic layer was washed successively with an ice-cooled saturated aqueous solution of potassium hydrogen sulfate (30 ml, twice), ice-water (30 ml), an ice-cooled saturated aqueous solution of sodium hydrogen carbonate (30 ml) and ice-water (30 ml) and then dried over anhydrous magnesium sulfate. The solvent was distilled off under reduced pressure to give 2.13 g (100%) of the title compound as a pale yellow foamy substance.

IR (KBr tablet method) cm$^{-1}$: 1771, 1710.

NMR (CDCl$_3$) δ ppm: 1.52 (9H, s), 1.81 (3H, d, J=6 Hz), 2.08 (3H, s), 3.19 (1H, d, J=18 Hz), 3.50 (1H, d, J=18 Hz), 4.4~4.9 (1H, m), 5.15 (1H, d, J=5 Hz), 5.42 (1H, dd, J=5 Hz, 2 Hz), 8.15+8.17 (1H, d+d, J=2 Hz).

EXAMPLE 1

Benzhydryl 7β-(2′-chloro-2′-butenylideneamino)-7α-methoxy-3-(1-methyl-1H-tetrazol-5-yl)thiomethyl-3-cephem-4-carboxylate

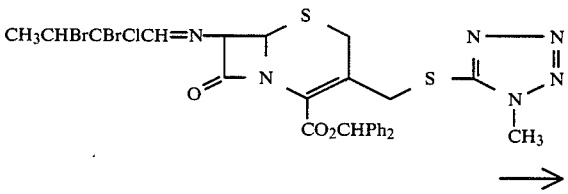

-continued

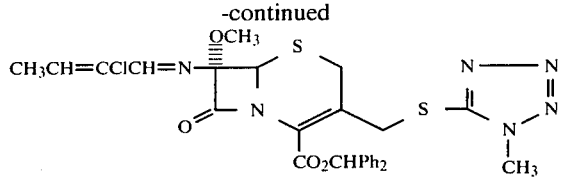

To benzhydryl 7β-(2',3'-dibromo-2'-chlorobutylideneamino)-3-(1-methyl-1H-tetrazol-5-yl)thiomethyl-3-cephem-4-carboxylate (0.370 g, 0.500 mmol) and borax (Na$_2$B$_4$O$_7$.10H$_2$O) (0.572 g, 1.500 mmol) was added a mixture of acetonitrile (10 ml) and methanol (5 ml) under ice-cooling and the mixture was stirred under ice-cooling for 4 hours. Then, the reaction mixture was added to a saturated aqueous solution of sodium chloride (30 ml) under ice-cooling and the mixture was extracted with ethyl acetate (20 ml, twice). The organic layer was washed with a saturated aqueous solution of sodium chloride (30 ml) and then dried over anhydrous magnesium sulfate. After concentrating under reduced pressure, the residue was separated and purified by a silica gel thin-layer chormatography to afford 0.230 g (75%) of the title compound as a pale yellow crystal. Rf value=0.65 (benzene:ethyl acetate=5:1).

m.p.=103.5°~104.5° C.

IR (KBr tablet method) cm$^{-1}$: 1775, 1721, 1630

NMR (CDCl$_3$) δ ppm: 1.95 (1H, d, J=6 Hz), 3.46 (3H, s), 3.55 (2H, broad s), 3.67 (3H, s), 4.09 (1H, d, J=14 Hz), 4.36 (1H, d, J=14 Hz), 4.97 (1H, s), 6.41 (1H, q, J=6 Hz), 6.79 (1H, s), 7.05~7.50 (10H, m), 8.03 (1H, s).

MS (FD) m/e: 610 (M+)

EXAMPLE 2 tert-Butyl 7β-(2'-chloro-2'-butenylideneamino)-7α-methoxy-3-acetoxymethyl-3-cephem-4-carboxylate

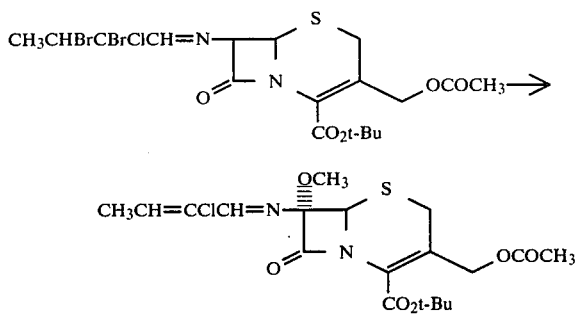

To tert-butyl 7β-(2',3'-dibromo-2-chlorobutylideneamino)-3-acetoxymethyl-3-cephem-4-carboxylate (200 mg, 0.348 mmol) and borax (Na$_2$B$_4$O$_7$.10H$_2$O) (0.398 g, 1.044 mmol) was added a mixture of methylene chloride (3 ml) and methanol (3 ml) and the resulting mixture was stirred at room temperature for 1.5 hours. The reaction mixture was concentrated to 1 ml, methylene chloride (20 ml) was added thereto and insolubles were filtered off. The filtrate was concentrated and the residue was separated by a silica gel thin-layer chromatography to give 106 mg (68%) of the title compound as a pale yellow foamy substance. Rf value=0.6 (benzene:ethyl acetate=17:3)

IR (KBr tablet method) cm$^{-1}$: 1780, 1738, 1720, 1632.

NMR (CDCl$_3$) δ ppm: 1.53 (9H, s), 2.01 (3H, d, J=6 Hz), 2.03 (3H, s), 3.25 (1H, d, J=18 Hz), 3.55 (1H, d, J=18 Hz), 3.54 (3H, s), 4.76 (1H, d, J=14 Hz), 5.02 (1H, d, J=14 Hz), 5.04 (1H, s), 6.59 (1H, q, J=6 Hz), 8.17 (1H, s).

MS (FD) m/e: 444 (M+)

EXAMPLE 3

Benzhydryl 7β-(2'-bromoallylideneamino)-7α-methoxy-3-(1-methyl-1H-tetrazol-5-yl)thiomethyl-3-cephem-4-carboxylate

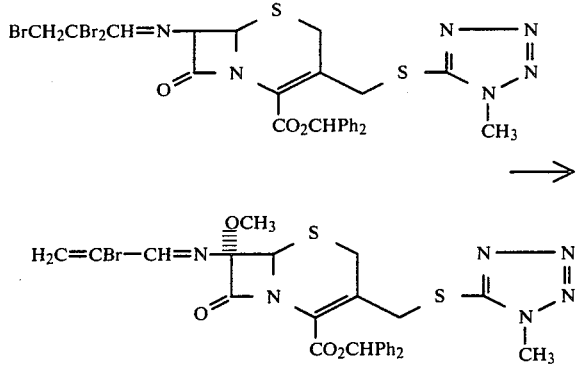

To a solution of benzhydryl 7β-(2',2',3'-tribromopropylideneamino)-3-(1-methyl-1H-tetrazol-5-yl)thiomethyl-3-cephem-4-carboxylate (0.386 g, 0.500 mmol) in tetrahydrofuran (10 ml) was added dropwise at −78° C. a methanolic solution of lithium methoxide (1.5 mmol) prepared from lithium (0.010 g) and methanol (3 ml). After stirring at −78° C. for 15 minutes, acetic acid (0.3 ml) was added to the reaction mixture, which was then poured into a mixture of a saturated aqueous solution of sodium hydrogen carbonate (20 ml) and ice (20 g) followed by extracting with methylene chloride (30 ml, twice). The organic layer was dried over anhydrous magnesium sulfate, concentrated under reduced pressure and the residue was separated and purified by a silica gel thin-layer chromatography to afford 0.164 g (51%) of the title compound as a pale yellow foamy substance. Rf value=0.65 (benzene:ethyl acetate=4:1).

NMR (CDCl$_3$) δ ppm: 3.48 (3H, s), 3.53 (2H, broad s), 4.13 (1H, d, J=14 Hz), 4.41 (1H, d, J=14 Hz), 5.00 (1H, s), 6.32 (1H, d, J=2 Hz), 6.38 (1H, d, J=2 Hz), 6.80 (1H, s), 7.05~7.50 (10H, m), 7.94 (1H, s).

EXAMPLE 4

Benzhydryl 7β-(2'-bromocinnamylideneamino)-7α-methoxy-3-(1-methyl-1H-tetrazol-5-yl)thiomethyl-3-cephem-4-carboxylate

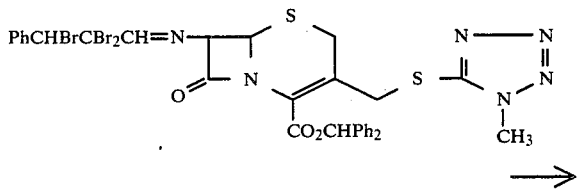

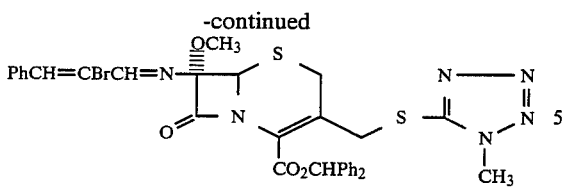

To a mixture of benzhydryl 7β-(2',2',3'-tribromo-3'-phenylpropylideneamino)-3-(1-methyl-1H-tetrazol-5-yl)-thiomethyl-3-cephem-4-carboxylate (0.400 g, 0.472 mmol) and borax ($Na_2B_4O_7 \cdot 10H_2O$) (0.540 g, 1.416 mmol) was added a mixture of methanol (5 ml) and methylene chloride (5 ml) and the resulting mixture was stirred at room temperature for 30 minutes. The reaction mixture was stirred well with methylene chloride (10 ml) and insoluble were filtered off. The methylene chloride solution was concentrated and the residue was separated and purified by a silica gel thin-layer chromatography to afford 0.241 g (71%) of the title compound as a pale yellow foamy substance. Rf value=0.65 (benzene:ethyle acetate=4:1).

IR (KBr tablet method) $cm^{-1}$: 1780, 1721, 1620, 1602.

NMR ($CDCl_3$) δ ppm: 3.51 (3H, s), 3.59 (2H, broad s), 3.68 (3H, s), 4.16 (1H, d, J=14 Hz), 4.36 (1H, d, J=14 Hz), 5.02 (1H, s), 6.81 (1H, s), 6.95~7.80 (16H, m), 8.11 (1H, s).

EXAMPLE 5

Benzhydryl 7β-(2'-chloro-2'-butenylideneamino)-7α-methoxy-3-(1-methyl-1H-tetrazol-5-yl)thiomethyl-3-cephem-4-carboxylate

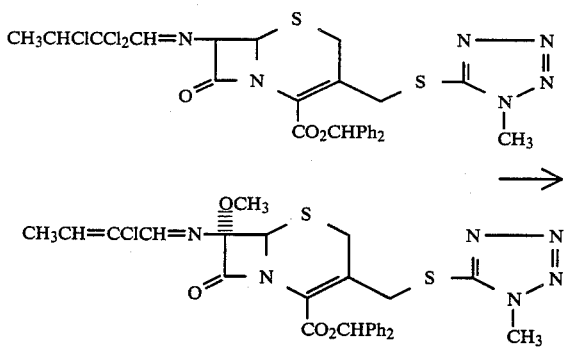

To a solution of benzhydryl 7β-(2',2',3'-trichlorobutylideneamino)-3-(1-methyl-1H-tetrazol-5-yl)thiomethyl-3-cephem-4-carboxylate (0.326 g, 0.500 mmol) in tetrahydrofuran (10 ml) was added at −78° C. a methanolic solution of lithium methoxide (0.5 mmol) prepared from lithium (0.003 g) and methanol (3 ml) and the resulting mixture was stirred for 10 minutes and then acetic acid (0.08 ml) was added thereto. The reaction mixture was added to a saturated aqueous solution of sodium hydrogen carbonate (20 ml) under ice-cooling and the mixture was then extracted with ethyl acetate (20 ml, twice). The organic layer was washed with a saturated aqueous solution of sodium chloride (20 ml) and then dried over anhydrous magnesium sulfate. After concentrating under reduced pressure, the residue was separated and purified by a column chromatography in the same manner as in the Example 2 to give the title compound, the melting point and spectra of which were in agreement with those obtained in the Example 2.

EXAMPLE 6 tert-Butyl 7β-(2'-chloro-2'-butenylideneamino)-7α-methoxy-3-methyl-3-cephem-4-carboxylate

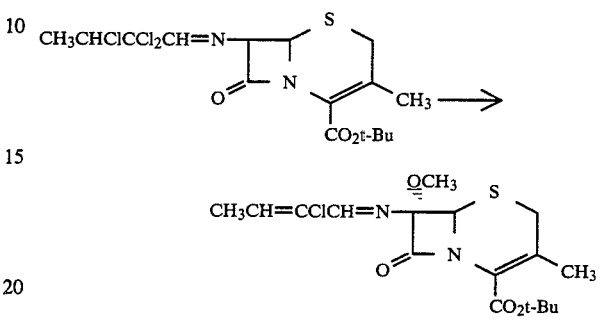

To a solution of tert-butyl 7β-(2',2',3'-trichlorobutylideneamino)-3-methyl-3-cephem-4-carboxylate (200 mg, 0.470 mmol) in tetrahydrofuran (5 ml) was added at −78° C. a methanolic solution of lithium methoxide (1.4 mmol) prepared from lithium (0.01 g) and methanol (3 ml) and the resulting mixture was stirred at −50° C. for 30 minutes. To the reaction mixture was added acetic acid (0.2 ml) and a temperature was allowed to raise to 0° C. The reaction mixture was added to an ice-cooled saturated aqueous solution of sodium hydrogen carbonate (20 ml) and the mixture was extracted with ethyl acetate (20 ml, twice). The organic layer was washed with a saturated aqueous solution of sodium chloride (20 ml) and then dried over anhydrous magnesium sulfate. After concentrating under reduced pressure, the residue was separated by a silica gel thin-layer chromatography to give 129 mg (71%) of the title compound as a pale yellow foamy substance. Rf value=0.70 (benzene:ethyl acetate=10:1).

IR (KBr tablet method) $cm^{-1}$: 1770, 1710, 1630.

NMR ($CDCl_3$) δ ppm: 1.53 (9H, s), 2.06 (3H, d, J=6 Hz), 2.09 (3H, s), 3.17 (1H, d, J=18 Hz), 3.47 (1H, d, J=18 Hz), 3.60 (3H, s), 5.06 (1H, s), 6.60 (1H, q, J=6 Hz), 8.20 (1H, s).

SYNTHESIS EXAMPLE 7

Benzhydryl 7β-(bromoacetylamino)-7α-methoxy-3-(1-methyl-1H-tetrazol-5-yl)thiomethyl-3-cephem-4-carboxylate

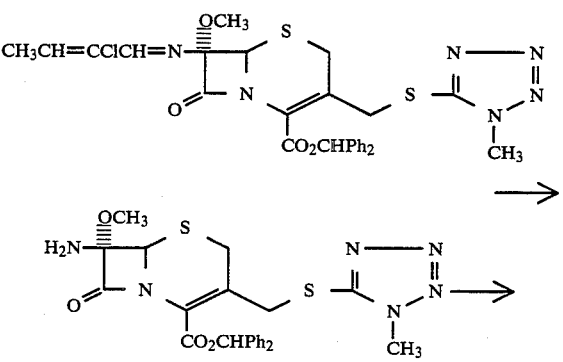

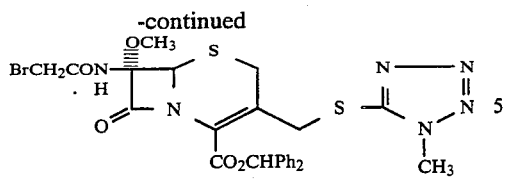

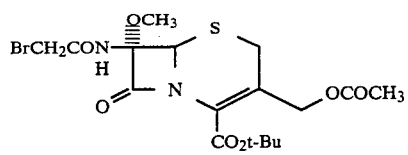

(1) To a solution of benzhydryl 7β-(2′-chloro-2′-butenylideneamino)-7α-methoxy-3-(1-methyl-1H-tetrazol-5-yl)thiomethyl-3-cephem-4-carboxylate (0.200 g, 0.327 mmol) in ethyl acetate (7 ml) was added a solution of (carboxymethyl)trimethyl ammonium chloride hydrazide (hereinafter referred to as Girard T reagent) and acetic acid (0.19 ml) in methanol (10 ml) and the resulting mixture was stirred under ice-cooling for 4.5 hours. To the reaction mixture was added a mixture of a saturated solution of sodium hydrogen carbonate (20 ml) and ice (20 g) and the resulting mixture was extracted with ethyl acetate (20 ml, twice). The organic layer was washed with ice-water (20 ml, twice) and dried over anhydrous magnesium sulfate to give a solution of benzhydryl 7β-amino-7α-methoxy-3-(1-methyl-1H-tetrazol-5-yl)thiomethyl-3-cephem-4-carboxylate in ethyl acetate.

(2) The ethyl acetate solution obtained in the above (1) was concentrated under reduced pressure to 10 ml, ethyl actate (30 ml) was added thereto and the mixture was again concentrated under reduced pressure to 5 ml. To the concentrated solution were added at −20° C. N,N-dimethylaniline (0.070 ml, 0.55 mmol) and then bromoacetyl bromide (0.050 ml, 0.55 mmol). The reaction mixture was stirred under ice-cooling for 10 minutes and, after addition of ice-water (30 ml), was extracted with ethyl acetate (50 ml). The ethyl acetate layer was washed successively with an ice-cooled saturated aqueous solution of potassium hydrogen sulfate (20 ml, thrice), ice-water (20 ml), an ice-cooled saturated aqueous solution of sodium hydrogen carbonate (20 ml) and a saturated aqueous solution of sodium chloride and then dried over anhydrous magnesium sulfate. After removal of the solvent under reduced pressure, the residue was separated and purified by a silica gel thin-layer chromatogrphy to afford 0.135 g (64%) of the title compound as a white crystal. The melting point, IR spectra and NMR spectra thereof were in fair agreement with those as stated in the literature (Japanese Laid-Open Patent Application No. 30196/1979).

SYNTHESIS EXAMPLE 8 tert-Butyl 7β-(bromoacetylamino)-7α-methoxy-3-acetoxymethyl-3-cephem-4-carboxylate

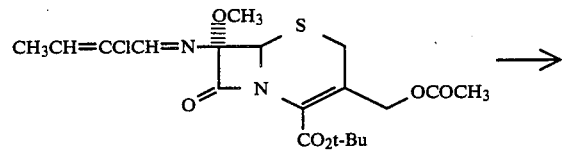

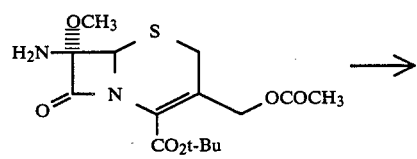

(1) To a solution of tert-butyl 7β-(2′-chloro-2′-butenylideneamino)-7α-methoxy-3-acetoxymethyl-3-cephem-4-carboxylate (100 mg, 0.225 mmol) in ethyl acetate (4 ml) was added a solution of Girard T reagent (113 mg, 0.675 mmol) and acetic acid (0.13 ml) in methanol (4 ml) and the resulting mixture was stirred at room temperature for 2 hours. The reaction mixture was added to an ice-cooled saturated aqueous solution of sodium hydrogen carbonate (20 ml) and the resulting mixture was extracted with ethyl acetate (20 ml, twice). The organic layer was washed with ice-water (20 ml, twice) and dried over anhydrous magnesium sulfate to give a solution of tert-butyl 7β-amino-7α-methoxy-3-acetoxymethyl-3-cephem-4-carboxylate in ethyl acetate.

(2) The ethyl acetate solution of the amino ester obtained in the above (1) was subjected to bromoacetylation in the same manner as in the Synthesis Example 7-(2) to give 54 mg (50%) of the title compound as a white foamy substance.

IR (KBr tablet method) cm$^{-1}$: 3300, 1780, 1722.

NMR (CDCl$_3$) δ ppm: 1.54 (9H, s), 2.03 (3H, s), 3.22 (1H, d, J=18 Hz), 3.43 (1H, d, J=18 Hz), 3.52 (3H, s), 3.86 (2H, s), 4.71 (1H, d, J=14 Hz), 4.90 (1H, d, J=14 Hz), 4.98 (1H, s), 7.15 (1H, broad s).

SYNTHESIS EXAMPLE 9

Benzhydryl 7β-(2′,3′-dibromo-2′-ethylbutylideneamino)-3-(1-methyl-1H-tetrazol-5-yl)thiomethyl-3-cephem-4-carboxylate

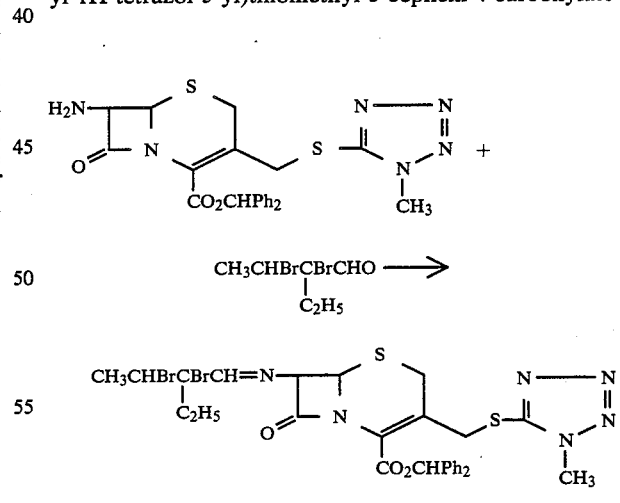

To a solution of benzhydryl 7β-amino-3-(1-methyl-1H-tetrazol-5-yl)thiomethyl-3-cephem-4-carboxylate (2.47 g, 5.00 mmol) in methylene chloride (35 ml) was added under ice-cooling a solution of 2,3-dibromo-2-ethylbutanal (1.42 g, 5.50 mmol) in methylene chloride (5 ml) followed by addition of anhydrous magnesium sulfate. The resulting mixture was stirred at room temperature for 4 hours. The reaction mixture was filtered, the filtrate was concentrated under reduced pressure and, after addition of benzene (20 ml) and thorough stirring, insolubles were filtered off. The filtrate was concentrated to dryness under reduced pressure and the reside was made powdery by the addition of ether (10 ml). The resulting powder was recovered by filtration and dried under reduced pressure to give 3.12 g (85%) of the title compound as a pale brown powder.

IR (KBr tablet method) cm$^{-1}$: 1780, 1718.

NMR (CDCl$_3$) δ ppm: 1.03 (3H, t, J=7 Hz), 2.83+2.89 (3H, d+d, J=6 Hz), 2.0~2.5 (2H, m), 4.65 (2H, broad s), 3.79 (3H, s), 4.14 (1H, d, J=14 Hz), 4.43 (1H, d, J=14 Hz), 4.3~4.7 (1H, m), 4.96 (1H, d, J=5 Hz), 5.1~5.3 (1H, m), 6.80 (1H, s), 7.30 (10H, broad s), 8.05~8.25 (1H, m).

EXAMPLE 7

Benzhydryl 7β-(2'-ethyl-2'-butenylideneamino)-7α-methoxy-3-(1-methyl-1H-tetrazol-5-yl)thiomethyl-3-cephem-4-carboxylate

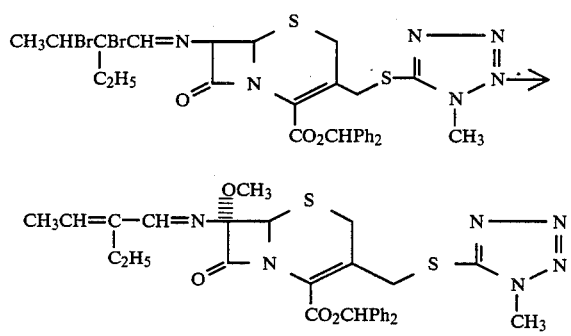

To a mixture of benzhydryl 7β-(2',3'-dibromo-2'-ethylbutylideneamino)-3-(1-methyl-1H-tetrazol-5-yl)thiomethyl-3-cephem-4-carboxylate (0.367 g, 0.500 mmol) and borax (Na$_2$B$_4$O$_7$.10H$_2$O) (0.572 g, 1.500 mmol) was added under ice-cooling a mixture of methanol (5 ml) and acetonitrile (10 ml) and the resulting mixture was stirred under ice-cooling for 2 hours and subsequently at room temperature for further one hour. The reaction mixture was added to a saturated aqueous solution of sodium chloride (30 ml) under ice-cooling and the resulting mixture was then extracted with ethyl acetate (20 ml, twice). The organic layer was washed with an ice-cooled aqueous solution of sodium chloride (20 ml) and dried over anhydrous magnesium sulfate. After concentrating under reduced pressure, the residue was separated by a silica gel thin-layer chromatography to afford 0.071 g (23%) of the title compound as a pale yellow foamy substance. Rf value=0.60 (benzene:ethyl acetate=5:1).

IR (KBr tablet method) cm$^{-1}$: 1775, 1720, 1615.

NMR (CDCl$_3$) δ ppm: 1.00 (3H, t, J=7 Hz), 1.81 (3H, d, J=7 Hz), 2.31 (2H, q, J=7 Hz), 3.43 (3H, s), 3.52 (2H, broad s), 3.69 (3H, s), 4.10 (1H, d, J=14 Hz), 4.30 (1H, d, J=14 Hz), 4.91 (1H, s), 6.01 (1H, q, J=7 Hz), 6.78 (1H, s), 7.0~7.5 (10H, m), 7.90 (1H, s).

SYNTHESIS EXAMPLE 10

Benzhydryl 7β-(2',2',3'-trichloro-3'-phenylpropylideneamino)-3-(1-methyl-1H-tetrazol-5-yl)thiomethyl-3-cephem-4-carboxylate

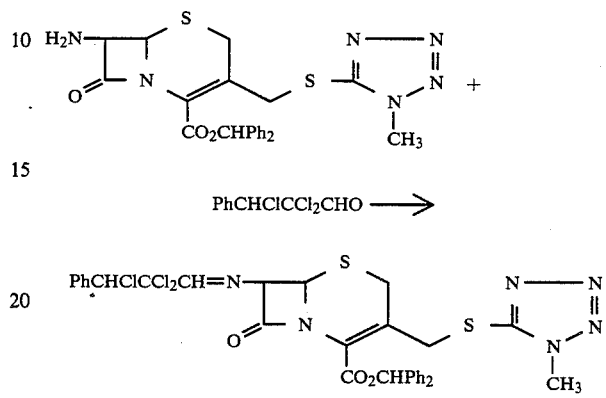

To a solution of benzhydryl 7β-amino-3-(1-methyl-1H-tetrazol-5-yl)thiomethyl-3-cephem-4-carboxylate (0.989 g, 2.000 mmol) in methylene chloride (25 ml) was added a solution of 2,2,3-trichloro-3-phenylpropanal (quantitatively prepared by the reaction of α-chlorocinnamaldehyde with an excess amount of bromine in methylene chloride) (0.570 g, 2.400 mmol) in methylene chloride (5 ml) and 15 ml of the solvent was distilled off in 2 hours while stirring with heating. To the reaction mixture was added methylene chloride (15 ml) and 10 ml of the solvent was again distilled off in 2 hours while stirring with heating. Again, 10 ml of methylene chloride were added to the reaction mixture and 10 ml of the solvent was distilled off in one hour while stirring with heating. The reaction mixture was concentrated under reduced pressure and the residue was separated by a flash column chromatography with Wakogel C300 (100 g) (benzene:ethyl acetate=10:1 as a developing solvent). Combined fractions of Rf value=0.65 (benzene:ethyl acetate=4:1) were concentrated to dryness under reduced pressure to give 1.200 g (Yield 84%) of the title compound as a colorless foamy substance.

IR (KBr tablet method) cm$^{-1}$: 1780, 1720.

NMR (CDCl$_3$) δ ppm: 3.59 (2H, broad s), 3.68 (3H, s), 4.09 (1H, d, J=14 Hz), 4.35 (1H, d, J=14 Hz), 4.96 (1H, d, J=5 Hz), 5.2~5.5 (2H, m), 6.77 (1H, s), 7.0~7.5 (10H, m), 7.99+8.07 (1H, d, J=2 Hz, +d, J=2 Hz).

EXAMPLE 8

Benzhydryl 7β-(2'-chlorocinnamylideneamino)-7α-methoxy-3-(1-methoxy-1H-tetrazol-5-yl)thiomethyl-3-cephem-4-carboxylate

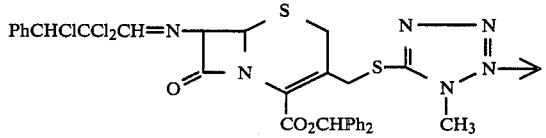

-continued

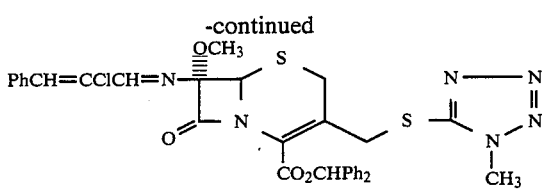

To a mixture of benzhydryl 7β-(2′,2′,3′-trichloro-3′-phenylpropylideneamino)-3-(1-methyl-1H-tetrazol-5-yl)thiomethyl-3-cephem-4-carboxylate (0.357 g, 0.500 mmol) and borax ($Na_2B_4O_7 \cdot 10H_2O$) (0.572 g, 1.500 mmol) was added a mixture of methanol (5 ml) and acetonitrile (5 ml) under ice-cooling and the resulting mixture was stirred under ice-cooling for 3 hours. The reaction mixture was added to an ice-cooled saturated aqueous solution of sodium chloride (20 ml) and the resulting mixture was extracted with ethyl acetate (20 ml, twice). The organic layer was dried over anhydrous magnesium sulfate and concentrated under reduced pressure. The residue was separated by a flash column chromatography employing Wakogel C300 (30 g) (benzene:ethyl acetate=10:1 as a developing solvent). Combined fractions of Rf=0.6 (benzene:ethyl acetate=4:1) were concentrated to dryness under reduced pressure to give 0.293 g (Yield 87%) of the title compound as a pale yellow foamy substance.

IR (KBr tablet method) $cm^{-1}$: 1778, 1720, 1605 (1610 shoulder)

NMR ($CDCl_3$) δ ppm: 3.49 (3H, s), 3.52 (2H, broad s), 3.66 (3H, s), 4.10 (1H, d, J=14 Hz), 4.34 (1H, d, J=14 Hz), 4.96 (1H, s), 6.80 (1H, s), 7.0~7.8 (16H, m), 8.28 (1H, s).

SYNTHESIS EXAMPLE 11

Benzhydryl 7β-(bromoacetylamino)-7α-methoxy-3-(1-methyl-1H-tetrazol-5-yl)thiomethyl-3-cephem-4-carboxylate

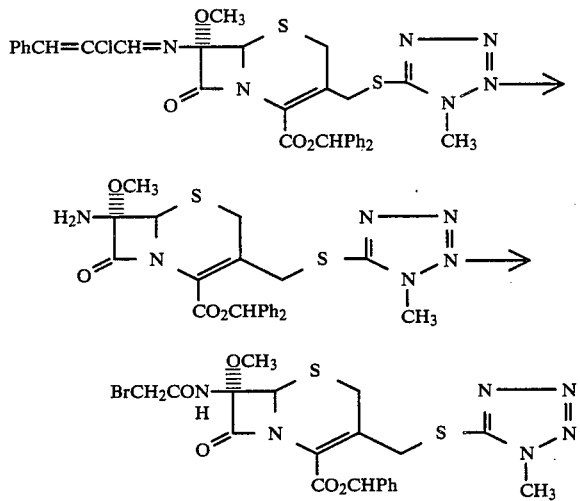

(1) To a solution of benzhydryl 7β-(2′-chlorocinnamylideneamino)-7α-methoxy-3-(1-methyl-1H-tetrazol-5-yl)thiomethyl-3-cephem-4-carboxylate (0.290 g, 0.431 mmol) in ethyl acetae (7 ml) was added under ice-cooling a solution of Girard T reagent (0.361 g, 2.15 mmol) and acetic acid (0.25 ml) in methanol (14 ml) and the resulting mixture was stirred under ice-cooling for 4 hours. The reaction mixture was added to an ice-cooled saturated aqueous solution of sodium hydrogen carbonate (30 ml) and the resulting mixture was extracted with ethyl acetate (20 ml, twice). The organic layer was washed with ice-water (20 ml, twice) and dried over anhydrous magnesium sulfate to give a solution of benzhydryl 7β-amino-7α-methoxy-3-(1-methyl-1H-tetrazol-5-yl)thiomethyl-3-cephem-4-carboxylate in ethyl acetate.

(2) The ethyl acetate solution of the amino ester obtained in the above (1) was subjected to bromoacetylation in the same manner as in the Synthesis Example 7-(2) to give 0.201 g (72%) of the title compound as a white crystal. The melting point, IR spectra and NMR spectra thereof were in fair agreement with those obtained in the Synthesis Example 7 as well as with those of the literature (Japanese Laid-Open Patent Application No. 30196/1979).

We claim:

1. A cephem compound of the formula:

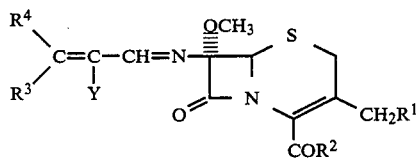

wherein $R^1$ represents a hydrogen atom or a group of —A—B in which A is an oxygen atom or a sulfur atom and B is an acyl group selected from the group consisting of an acetyl group and an acetoacetyl group; a heterocyclic group selected from the group consisting of a 1H-tetrazol-5-yl group, a 1-methyl-1H-tetrazol-5-yl group, a 1-carboxymethyl-1H-tetrazol-5-yl group, a 2-carboxymethyl-1H-triazol-5-yl group, a 1-sulfoethyl-1H-tetrazol-5-yl group, a 2-carboxymethyl-1-methyl-1H-triazol-5-yl group, a 1-sulfoethyl-1H-tetrazol-5-yl group, a 2-carboxymethyl-1-methyl-1H-triazol-5-yl group, a 4-methyl-5-oxo-6-hydroxy-4,5-dihydro-1,2,4-triazin-3-yl group, a pyridiniummethyl group, a triazolyl group and a thiadiazolyl group; or a carbamoyl group; $R^2$ is a hydroxy group or a carboxyl-protecting group; $R^3$ and $R^4$ may be the same or different and each represent a hydrogen atom, a lower alkyl group or a phenyl group; Y represents a halogen atom.

2. The cephem compound according to claim 1, wherein $R^1$ is an acetoxy group or a (1-methyl-1H-tetrazol-5-yl)thio group.

3. The cephem compound according to claim 1, wherein $R^2$ is a tert-butyl group or a benzhydryl group.

4. The cephem compound according to claim 1, wherein $R^1$ is an acetoxy group or a (1-methyl-1H-tetrazol-5-yl)thio group, Y is a chlorine atom and $R^2$ is a benzhydryl group.

5. A process for preparing a compound of the formula:

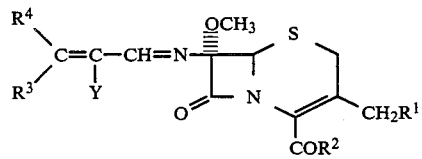

wherein $R^1$ represents a hydrogen atom or a group of —A—B in which A is an oxygen atom or a sulfur atom and B is an acyl group selected from the group consisting of an acetyl group and an acetoacetyl group; a heterocyclic group selected from the group consisting of a 1H-tetrazol-5-yl group, a 1-methyl-1H-tetrazol-5-yl group, a 1-carboxymethyl-1H-tetrazol-5-yl group, a 2-carboxymethyl-1H-triazol-5yl group, a 1-sulfoethyl-1H-tetrazol-5-yl group, a 2-carboxymethyl-1-methyl-1H-triazol-5-yl group, a 1-sulfoethyl-1H-tetrazol-5-yl group, a 2-carboxymethyl-1-methyl-1H-triazol-5-yl group, a 4-methyl-5-oxo-6-hydroxy-4,5-dihydro-1,2,4-triazin-3-yl group, a pyridiniummethyl group, a triazolyl group and a thiadiazolyl group; or a carbamoyl group; $R^2$ is a hydroxy group or a carboxy-protecting group; $R^3$ and $R^4$ may be the same or different and each represent a hydrogen atom, a lower alkyl group or a phenyl group; Y represents a halogen atom which comprises subjecting a cephem compound of the formula:

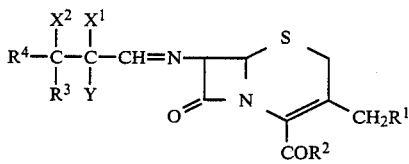

wherein $R^1$, $R^2$, $R^3$, $R^4$ and Y are as defined above, $X^1$ and $X^2$ may be the same or different and each represents a halogen atom; to the action of an acid binding agent selected from the group consisting of borax and alumina in the presence of methanol.

6. The process according to claim 5, wherein said acid binding agent is borax.

7. The process according to claim 5, wherein the reaction is carried out at room temperature to ice-cooling temperature.

* * * * *